(12) United States Patent
Guala

(10) Patent No.: US 6,673,059 B2
(45) Date of Patent: Jan. 6, 2004

(54) MALE LUER-LOCK CONNECTOR FOR MEDICAL FLUID LINES

(75) Inventor: Gianni Guala, Turin (IT)

(73) Assignee: Industrie Borla SpA, Turin (IT)

( * ) Notice: Subject to any disclaimer, the term of this patent is extended or adjusted under 35 U.S.C. 154(b) by 123 days.

(21) Appl. No.: 09/930,464

(22) Filed: Aug. 16, 2001

(65) Prior Publication Data

US 2002/0115984 A1 Aug. 22, 2002

(30) Foreign Application Priority Data

Feb. 16, 2001 (IT) ...................... TO2001A0140

(51) Int. Cl.[7] .................. A61M 25/16; F16L 49/00; F16L 25/00; F16L 35/00
(52) U.S. Cl. .................. 604/533; 285/256; 285/332
(58) Field of Search .................. 604/167.01–167.06, 604/533, 256, 905, 111, 255, 535; 285/332–335, 92, 33.4

(56) References Cited

U.S. PATENT DOCUMENTS 5,620,427 A * 4/1997 Werschmidt et al. ....... 604/535
5,984,373 A * 11/1999 Fitoussi et al. ............. 285/332
6,200,262 B1 * 3/2001 Ouchi ........................ 600/154
6,260,890 B1 * 7/2001 Mason ........................ 285/332

FOREIGN PATENT DOCUMENTS

GB 2 055 166 A 2/1981

* cited by examiner

Primary Examiner—Michael J. Hayes
Assistant Examiner—Roz GhaFoorian
(74) Attorney, Agent, or Firm—Sughrue Mion, PLLC

(57) ABSTRACT

A male luer-lock connector (1) for medical fluid lines comprising an elongated tubular body (2) with an end portion with external luer cone (10) and an internally threaded bushing mounted so that it can turn and slide on a portion with a cylindrical external surface (9) of the tubular body (2). The axial travel of advance (C) of the bushing (3) has a reduced length, and the portion with a cylindrical external surface (9) of the tubular body (2) has an annular widened portion (13) that can be elastically engaged by friction by the bushing (3) upon screwing of the latter on a female luer-lock connector (L).

9 Claims, 4 Drawing Sheets

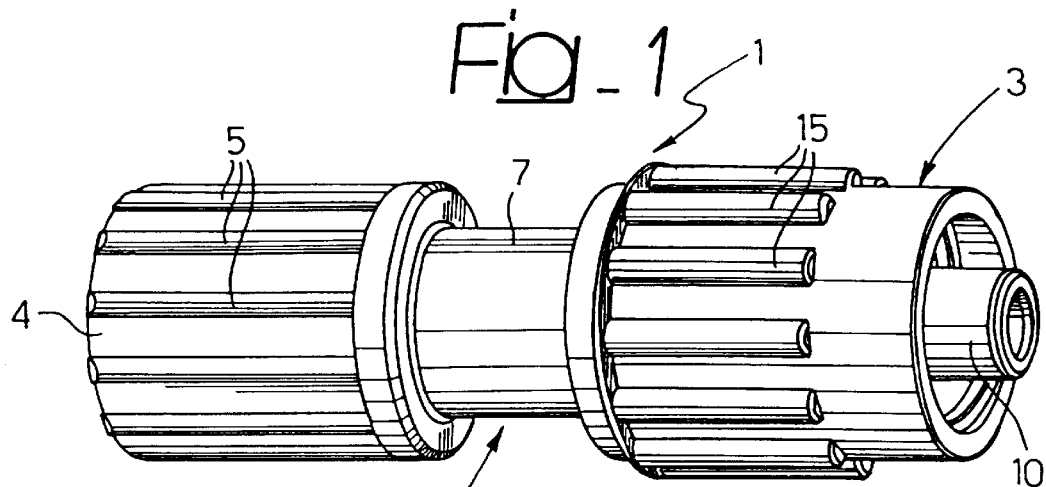
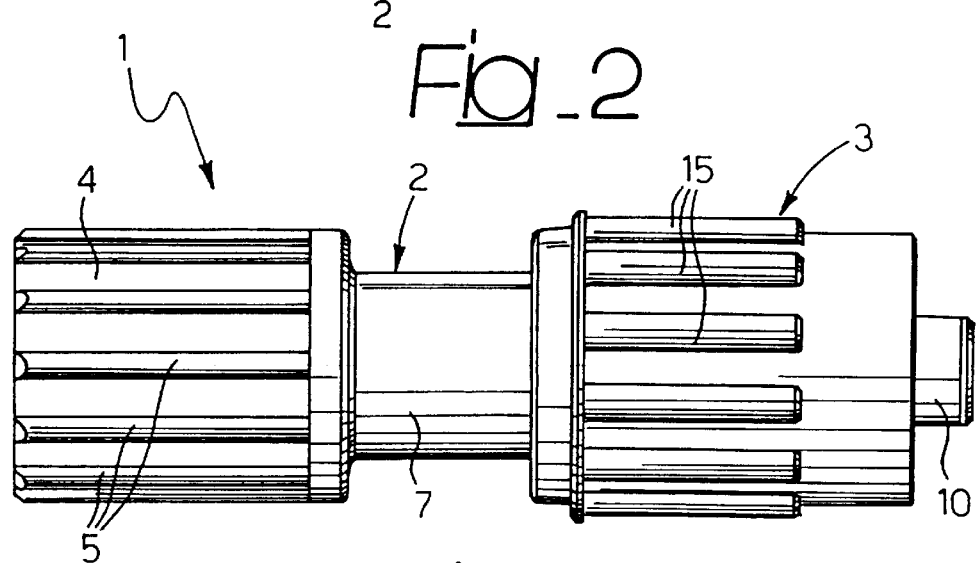
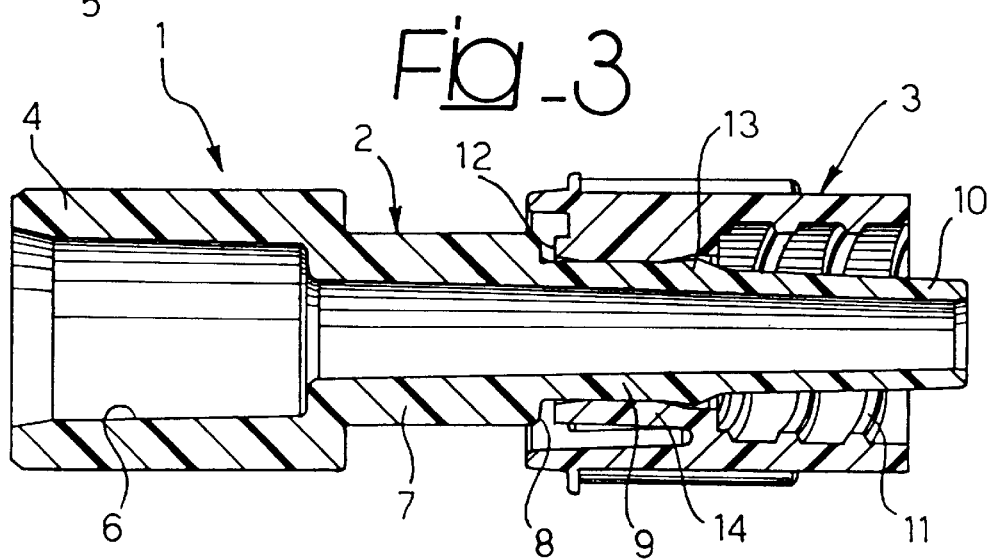

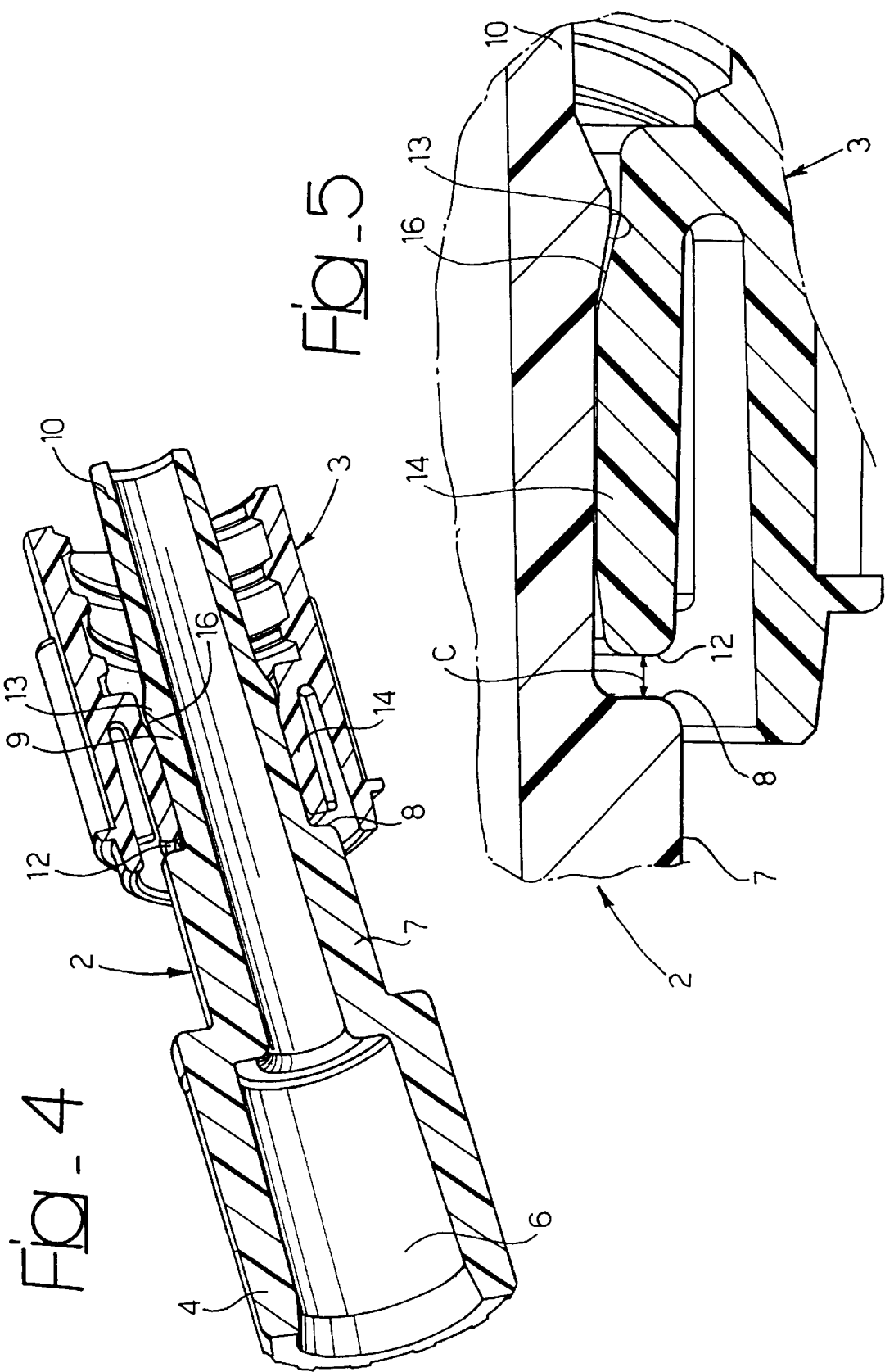

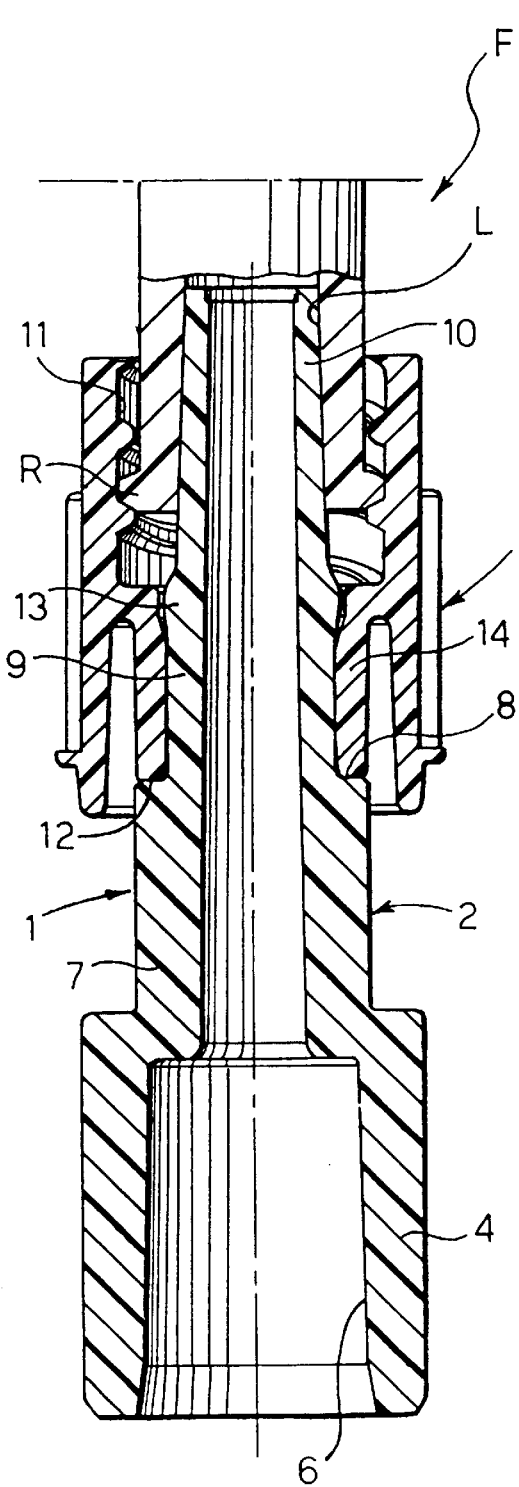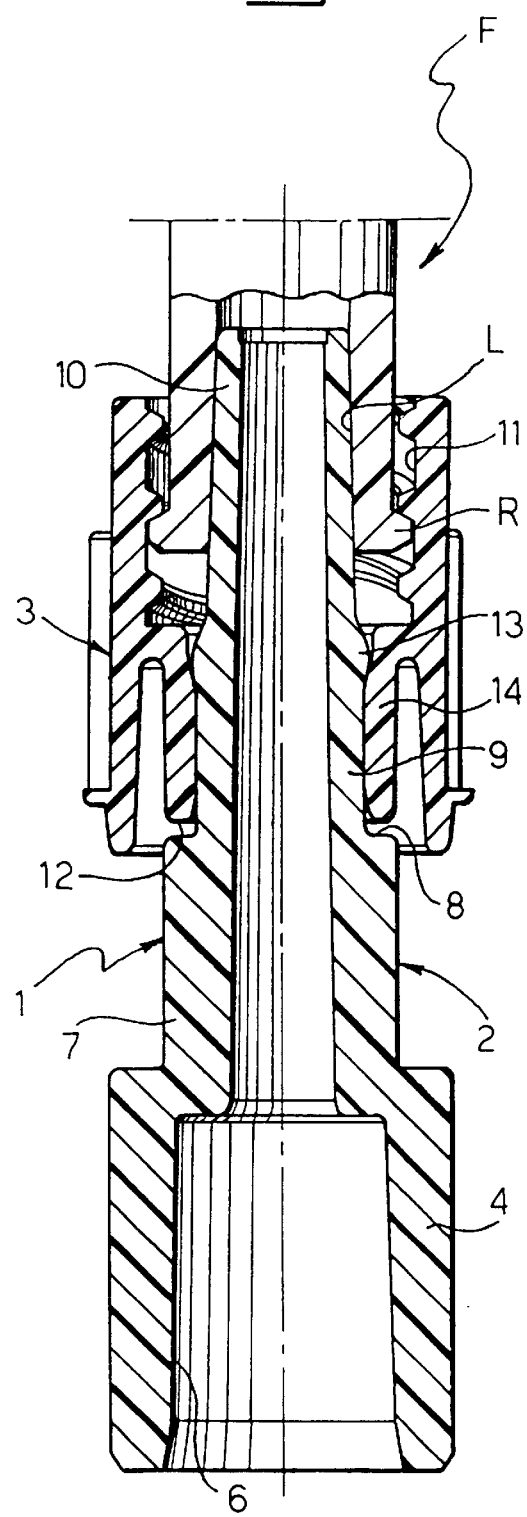

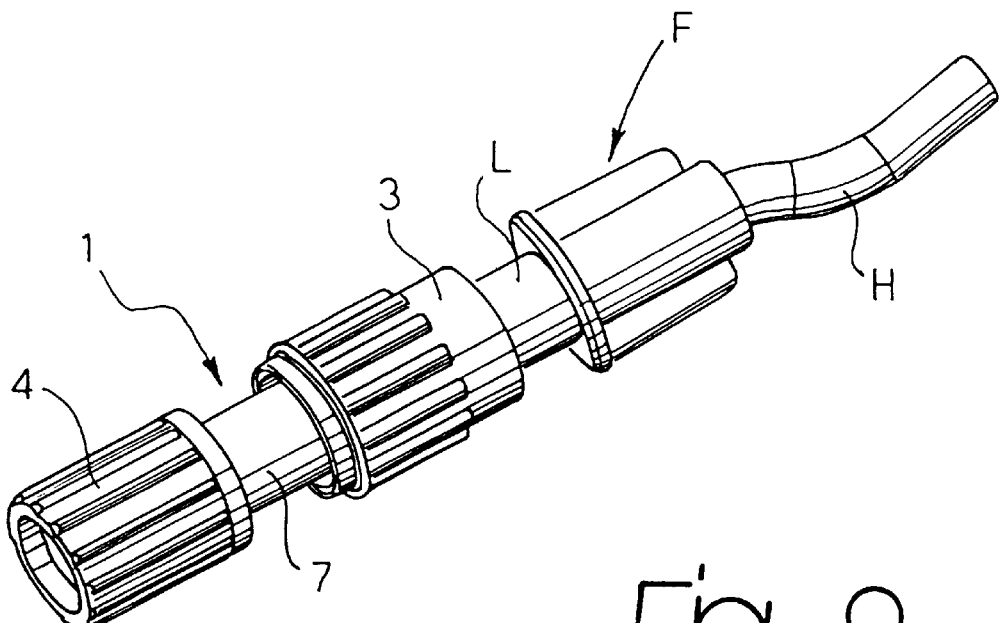
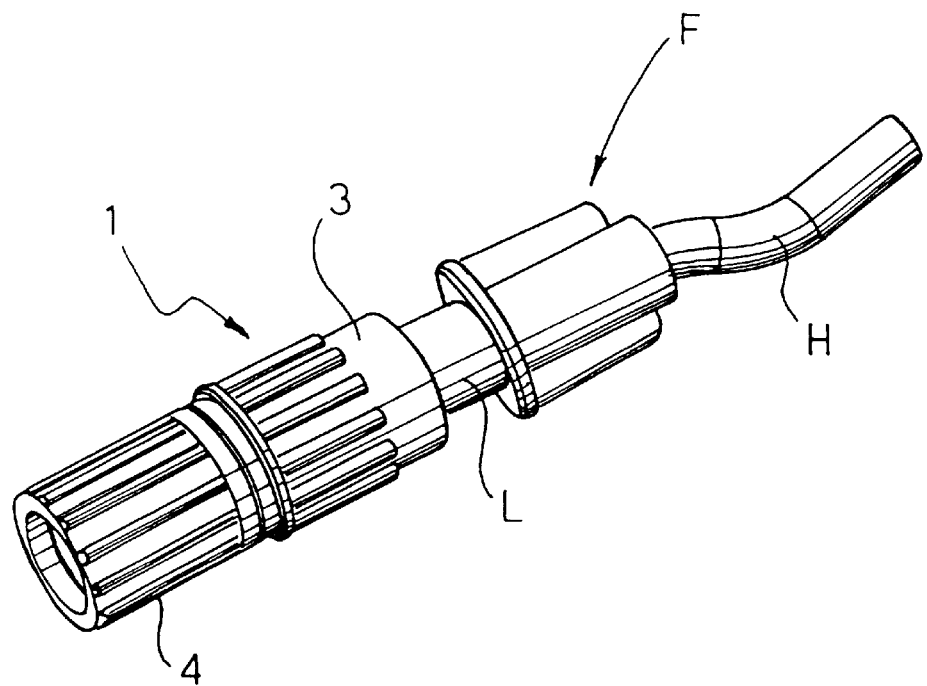

MALE LUER-LOCK CONNECTOR FOR MEDICAL FLUID LINES

BACKGROUND OF THE INVENTION

The present invention relates in general to connectors for medical fluid lines, and regards more in particular a male luer-lock connector of the type comprising an elongated tubular body having a portion with a cylindrical external surface and an end portion with external luer cone, and a bushing having an internal thread with which a female luer-lock connector can be screwed, the end portion with external luer cone of the tubular body being designed to engage in said female luer-lock connector.

Traditionally, the bushing is fixed with respect to the tubular body since it is integral with the portion having a cylindrical external surface of said tubular body. More recently, solutions have been proposed in which the bushing is mounted on the portion having a cylindrical external surface of the tubular body in such a way that it can turn and slide for an axial travel of advance of definite length starting from a drawn-back position.

This construction has the advantage that the male luer-lock connector can be connected and fastened to the female luer-lock connector, and released and detached from the latter without it being necessary to rotate the tubular body, and hence without any deformation or twisting of the flexible tubing or hose of the medical line attached, on one side, to the male connector and, on the other, to the female connector.

However, the above solutions with a bushing that can turn and slide has a series of drawbacks. In the first place, there is the risk that inexpert or distracted operators might make the connection between the male connector and the female connector in a wrong way, merely engaging axially the respective luer cones without screwing, or at least without screwing right down, the bushing on the female luer-lock connector. This involves the danger of accidental separation between the male connector and the female connector, which might have serious consequences for the patient to whom the medical line is applied.

An additional drawback of the aforesaid known solutions lies in the relative facility with which the male luer-lock connector detaches from the female luer-lock connector in the condition where the bushing is screwed right down on account of the modest force necessary to overcome the unscrewing torque. This may also lead to undesired or accidental detachment of the male luer-lock connector from the female luer-lock connector.

SUMMARY OF THE INVENTION

The object of the present invention is to overcome the above-mentioned drawbacks and to provide a male luer-lock connector of the type defined at the beginning of the present description, with a bushing which is able to turn and slide and which is shaped, on the one hand, in such a way as to prevent loose connections or, in any case, incorrect connections of the male connector to the female connector and, on the other hand, to prevent their accidental detachment, by increasing the amount of the initial unscrewing torque of the bushing.

According to the invention, the above purposes are achieved by means of a male luer-lock connector of the type defined in the introductory part of claim 1 and presenting the combination of characteristics listed in the characterizing part of claim 1. These characteristics are the following:

the axial travel of the bushing is of a short length and such as not to enable firm engagement of said end portion with external luer cone of the body of the male luer-lock connector on said female luer-lock connector, without screwing at least partially the internal thread of the bushing on the female luer-lock connector; and the portion with cylindrical external surface of the tubular body of the male luer-lock connector has an annular widened portion that can be elastically engaged by friction by said bushing upon screwing of the internal thread of the latter on said female luer-lock connector.

Thanks to this idea of solution, important advantages are achieved in terms of safety and operating reliability of the connector, which are summed up in what follows.

In the first place, connection of the male luer-lock connector to the female luer-lock connector by stable engagement between the corresponding luer cones cannot be obtained except following upon an at least partial screwing of the threaded bushing. This fact prevents an inexpert or distracted operator from possibly omitting to screw the bushing, but instead encourages him or her to screw it right down following upon the need for an initial screwing.

In the second place, in the condition where the bushing is screwed onto the female luer-lock connector, the interaction between said bushing and the annular widening of the cylindrical portion of the body increases their surface of mutual contact, and hence their cohesion, so guaranteeing a stable union between the male luer-lock connector and the female luer-lock connector, not only in the condition where the bushing is completely screwed, but also if the latter is screwed only partially.

The above effect is further accentuated if, as may be advantageously envisaged by the invention, the aforesaid annular widening of the cylindrical portion of the tubular body of the connector has a conical surface which diverges towards said end portion with luer cone.

In addition, the elastic reaction between the bushing and the annular widened portion of the cylindrical portion of the body functions as a brake and also enables accidental or undesired unscrewing of the bushing to be avoided, and hence prevents involuntary disconnection between the male luer-lock connector and the female luer-lock connector thanks to an appreciable increase in the initial unscrewing torque, and hence in the force necessary to overcome said torque.

In brief, the male luer-lock connector according to the invention has, as compared to similar currently known connectors, features of greater safety and reliability.

BRIEF DESCRIPTION OF THE DRAWINGS

The invention will now be described in detail with reference to the annexed drawings, which are provided purely by way of non-limiting example, and in which:

FIG. 1 is a schematic perspective view of a male luer-lock connector for medical fluid lines, according to the invention;

FIG. 2 is a side elevation of FIG. 1;

FIG. 3 is a longitudinal cross-sectional view of FIG. 2;

FIG. 4 is a perspective view of FIG. 3;

FIG. 5 shows a detail of FIG. 3 at a more enlarged scale;

FIG. 6 is similar to FIG. 3 and shows an assembly formed following upon the connection of the male luer-lock connector according to the invention to a female luer-lock connector in a condition prior to their being screwed together right down;

FIG. 7 is a view similar to FIG. 6 in the condition where the male luer-lock connector and the female luer-lock connector are completely fastened together;

FIG. 8 is a schematic perspective view at a reduced scale of the assembly represented in FIGS. 6 and 7; and FIG. 9 is a variant of FIG. 8.

DETAILED DESCRIPTION OF THE INVENTION

With reference initially to FIGS. 1 to 4, the number 1 generically designates a male luer-lock connector according to the invention for medical fluid lines, for example for haemodialysis.

The male luer-lock connector 1 is made up of two components, both of which are made of moulded plastic material: an elongated tubular body 2 and a threaded bushing 3.

The elongated tubular body 2 includes, in a single piece, an initial manoeuvring part 4, which is provided with longitudinal gripping projections 5, and the cavity of which, designated by 6, is designed for attachment thereto of the end of a flexible tubing or hose (not illustrated in the drawings). The manoeuvring part 4 is followed by an intermediate cylindrical part 7, which is in turn joined, via a radial annular shoulder 8, to a portion with a cylindrical surface 9 of smaller diameter. The portion with a cylindrical external surface 9 connects to an end portion with external luer cone 10.

As will be seen in what follows, the cylindrical intermediate part 7 can be omitted, and, in this case, the annular shoulder 8 will coincide with the edge of the manoeuvring part 4 facing the end portion with external luer cone 10.

The bushing 3 has an internal thread 11 and, externally, a series of axial manoeuvring projections 15. The said bushing 3 is mounted on the portion with a cylindrical external surface 9 of the tubular body 2 in such a way that it can both turn and axially slide for a travel of axial advance of definite length starting from a drawn-back position. The said drawn-back position is defined by the axial arrest between a front end edge 12 of the bushing 3 and the annular shoulder 8 of the tubular body 2.

According to one first fundamental characteristic of the invention, the length of said axial travel of advance of the bushing 3 is reduced and such that, as will be seen in what follows, it does not allow the end portion with luer cone 10 of the tubular body 2 to engage firmly within the internal luer cone of a complementary female luer-lock connector (which will be described hereinafter with reference to FIGS. 6 and 7) unless the internal thread 11 of the bushing 3 has been screwed at least partially beforehand on the female luer-lock connector. Purely by way of non-limiting example, with the standardized dimensions of luer-lock connectors of the type corresponding to the invention, the length of said travel, i.e., the amount of axial play of the bushing 3 on the tubular body 2, denoted by C in FIG. 5, is less than 0.5 mm and is more conveniently in the region of 0.3 mm.

According to another aspect of the invention, the travel of advance of the bushing 3 is delimited, on the side opposite to the annular shoulder 8, by an annular widened portion 13 formed on the portion with cylindrical external surface 9 of the tubular body 2 in the region of connection with the end portion with external luer cone 10. As may also be seen in detail in FIG. 5, the annular widened portion 13 conveniently has a conical surface which diverges towards the end portion with external luer cone 10. In the final stretch of the travel of advance of the bushing 3, the annular widened portion 13 can be engaged by friction (in the way represented in FIG. 7) by an elastically deformable internal portion 14 of the bushing 3. The said elastically deformable portion 14 has a conical internal surface 16 that is complementary to that of the annular widened portion 13 and may conveniently consist of a ring of integral axial sectors having the function of radial springs.

FIGS. 6 and 7 illustrate the modalities of connection/disconnection between the male luer-lock connector 1 according to the invention and a female luer-lock connector of a conventional type.

The said female luer-lock connector F comprises, in the usual way, a tubular body made of moulded plastic material designed for attachment of a flexible tubing or hose H, and an internal luer cone L, which is complementary to the end portion with external luer cone 10 of the male luer-lock connector 1, and is formed, at its free end, with external radial projections R, which can engage with the internal thread 11 of the bushing 3.

FIG. 6 illustrates a condition of loose engagement between the male connector 1 and the female connector F with the respective external luer cone 10 and internal luer cone L axially engaged together following upon engagement of the thread 11 on the projection R, but prior to screwing right down of the bushing 3. As may be seen, in this position the bushing 3 is drawn back on the portion with cylindrical external surface 9, with its front edge 12 substantially bearing upon the annular arrest shoulder 8.

Starting from this position, screwing right down of the thread 11 of the bushing 3 on the projections R of the female connector F produces, on the one hand, the axial forcing of the external luer cone 10 into the internal luer cone L and, on the other hand, the elastic engagement by friction of the elastically deformable portion 14 of the bushing 3 on the annular widened portion with conical surface 13 of the cylindrical portion 9 of the tubular body 2 in the way represented in FIG. 7. In this position, engagement of the male luer-lock connector 1 with the female luer-lock connector L is ensured in an absolutely stable and secure way thanks to the friction contact, and hence the cohesion, between the bushing 3 and the tubular body 2, thus preventing with the maximum degree of safety any risk of accidental disconnection due to movements, impact, thermal expansion, etc.

As regards the voluntary manoeuvre of disconnection of the male luer-lock connector 1 from the female luer-lock connector L, the elastic friction of the elastically deformable portion 14 of the bushing 3 on the annular widened portion having a conical surface 13 makes it possible to increase the value of the unscrewing torque between the internal thread 11 and the projections R, so preventing accidental unscrewing and enabling the said manoeuvre only in a voluntary way.

It should be noted that, in the event of the bushing 3 not being, for some reason, screwed on the female luer-lock connector L in a complete way during connection, or in any case in a way such as to achieve effective fastening by friction on the annular widened portion 13, a further possible loosening of the connection such as to reduce the mutual axial engagement between the external luer-lock cone 10 and the internal luer-lock cone L could not in any case lead to a complete separation in view of the fact that, even in this situation, the thread 11 of the bushing 3 would remain engaged with the projections R of the female connector F.

Disconnection between the male luer-lock connector 1 and the female luer-lock connector L is obtained by unscrewing of the bushing 3, which moves back until it stops against the shoulder 8 at the end of the axial travel C. Starting from this position, in which the thread 11 is, as has been said, in any case engaged with the projections R, the further rotation of unscrewing of the bushing 3 advantageously produces an action of self-extraction of the external luer cone 10 from the internal luer cone L until they are completely separated from one another.

Of course, the details of construction and the embodiments may vary widely with respect to what is described and illustrated herein, without thereby departing from the scope of the present invention as defined in the ensuing claims. Consequently, as has already been clarified previously, the cylindrical intermediate part 7 of the tubular body 2 of the connector 1 can be eliminated, the annular shoulder 8 in this case coinciding with the edge of the manoeuvring part 4 facing the end portion with external luer cone 10, in the way represented in FIG. 9.

What is claimed is:

1. A male luer-lock connector for medical fluid lines, comprising an elongated tubular body having a portion with a cylindrical external surface between a radial annular shoulder and an external luer cone end portion, and a bushing mounted on said portion with a cylindrical external surface of said tubular body so that it can turn and slide for an axial travel of advance of definite length starting from a drawn-back position defined by said shoulder, said bushing having an internal thread with which a female luer-lock connector can be screwed in which said external luer cone end portion of said tubular body is designed to engage axially, wherein:

said axial travel is of a short length and such as not to enable firm engagement of said external luer cone end portion of said body of said male luer-lock connector on said female luer-lock connector, without screwing at least partially said internal thread of said bushing on said female luer-lock connector;

said bushing has an inner axially extending elastically deformable portion movable in a radial direction; and said portion with cylindrical external surface of said tubular body of said male luer-lock connector has an annular widened portion that can be elastically engaged by friction by said elastically deformable portion of said bushing upon screwing of said internal thread of the latter on said female luer-lock connector.

2. The connector according to claim 1, wherein said annular widened portion has a conical surface diverging towards said external luer cone end portion.

3. The connector according to claim 2, wherein said bushing has a portion which is elastically deformable radially by said annular widened portion.

4. The connector according to claim 3, wherein said radially elastically deformable portion of said bushing has an internal conical surface complementary to the surface of said annular widened portion.

5. The connector according to claim 1, wherein the length of said axial travel is in the region of 0.3 mm.

6. A luer-lock connection assembly for medical fluid lines comprising a female luer-lock connector and a male luer-lock connector according to claim 1.

7. A male luer-lock connector for medical fluid lines, comprising an elongated tubular body having a portion with a cylindrical external surface and an external luer cone end portion, and a bushing mounted on said portion with a cylindrical external surface and an external tubular body so that it can turn and slide for an axial travel of advance of definite length starting from a drawn-back position, said bushing having an internal thread with which a female luer-lock connector can be screwed in which said external luer cone end portion of said tubular body is designed to engage axially, wherein:

said axial travel is of a short length and such as not to enable firm engagement of said external luer cone end portion of said body of said male luer-lock connector on said female luer-lock connector, without screwing at least partially said internal thread of said bushing on said female luer-lock connector; and said portion with cylindrical external surface of said tubular body of said male luer-lock connector has an annular widened portion that can be elastically engaged by friction by said bushing upon screwing of said internal thread of the latter on said female luer-lock connector, wherein said annular widened portion has a conical surface diverging towards said external luer cone end portion, wherein said bushing has an axially extending inner portion which is elastically deformable radially by said annular widened portion, and wherein said radially elastically deformable portion of said bushing has an internal conical surface complementary to the surface of said annular widened portion.

8. The connector according to claim 7, wherein the length of said axial travel is in the region of 0.3 mm.

9. A luer-lock connection assembly for medical fluid lines comprising a female luer-lock connector and a male luer-lock connector according to claim 1.

* * * * *